United States Patent
Palmer et al.

[11] Patent Number: 6,097,451
[45] Date of Patent: *Aug. 1, 2000

[54] LIQUID CRYSTAL SHUTTER WITH LOW TWISTED NEMATIC LIQUID CRYSTAL CELLS DRIVEN WITH A LOW FREQUENCY OR DC VOLTAGE

[75] Inventors: Stephen Palmer, Borlänge; Åke Hörnell, Mockfjärd, both of Sweden

[73] Assignee: Hornell International AB, Gagnet, Sweden

[*] Notice: This patent is subject to a terminal disclaimer.

[21] Appl. No.: 08/860,460
[22] PCT Filed: Oct. 25, 1996
[86] PCT No.: PCT/SE96/01372
    § 371 Date: Jun. 25, 1997
    § 102(e) Date: Jun. 25, 1997
[87] PCT Pub. No.: WO97/15254
    PCT Pub. Date: May 1, 1997

[30] Foreign Application Priority Data

Oct. 26, 1995 [SE] Sweden .................. 9503783

[51] Int. Cl.$^7$ .................................................. G02F 1/1337
[52] U.S. Cl. .................................. 349/14; 349/33; 349/77
[58] Field of Search .................................. 349/73, 75, 77, 349/14, 33

[56] References Cited

U.S. PATENT DOCUMENTS

| | | |
|---|---|---|
| 4,039,254 | 8/1977 | Harsch ........................... 349/14 |
| 5,111,317 | 5/1992 | Coulson . |
| 5,252,817 | 10/1993 | Fergason et al. ............... 250/205 |
| 5,298,688 | 3/1994 | Luechinger et al. ............ 177/181 |
| 5,315,099 | 5/1994 | Gunz et al. . |
| 5,347,383 | 9/1994 | Fergason ........................ 345/211 |
| 5,519,522 | 5/1996 | Fergason ........................ 349/14 |
| 5,825,441 | 10/1998 | Hornell et al. ................. 349/77 |

FOREIGN PATENT DOCUMENTS

WO 95/29428   11/1995   WIPO .

*Primary Examiner*—Kenneth Parker
*Attorney, Agent, or Firm*—Young & Thompson

[57] ABSTRACT

A liquid crystal shutter construction (18), suitable for a glass shield and a welding glass filter, which shutter construction is able to switch between a high light absorbing dark state and a low light absorbing transparent state, and vice versa, comprising low twisted nematic type liquid crystal cells with a twisting angle between 0° and just below 90°, and an electronic circuit output generating a variable cell driving voltage higher than about twice the threshold voltage for at least one of the liquid crystal cells and with a polarity switching frequency of less than 1 Hertz.

23 Claims, 5 Drawing Sheets

LIQUID CRYSTAL SHUTTER WITH LOW TWISTED NEMATIC LIQUID CRYSTAL CELLS DRIVEN WITH A LOW FREQUENCY OR DC VOLTAGE

The present invention relates to liquid crystal shutters suitable for electro-optical eye-protection devices, glare shields and automatically darkening welding glass filters.

BACKGROUND

Liquid crystal shutters are useful in various applications concerning the transmittance of light through an aperture in which it should be possible to switch the shutter between a low light-absorbing state with a low transmission density value and a high light-absorbing state with a high transmission density value. By combining polarisation filters and cells of liquid crystals that are alignable by means of an electric influence, the transmittance of state of the art liquid crystal shutters is made variable in response to a change in the electric influence.

This kind of shutters are favourably applied as light filters in for example eye-protection devices, such as automatically darkening welding glass shields. However, prior art liquid crystal shutters suffer from the problem that the transmission density is asymmetric and dependent on the angle of incidence of transmitted light. This angular dependence is due to an incomplete molecular alignment with the applied electric field when driven in an intermediate voltage range typically between 2 and 10 volts and is especially disadvantageous in applications that require a large field of view. Another problem is the high power consumption of such prior art shutters, which leads to rapidly consumed battery cells in mobile equipment and has well known economic as well as safety and environmental aspects.

A state of the art liquid crystal cell in this context consists of a liquid mixture of elongated molecules sandwiched between two delimiting glass plates. The liquid mixture facing surface layers of the glass plates are treated so that alignment directors, for example grooves, are formed having a uniform direction and the liquid crystal molecules close to such a surface layer tend to align parallel with the directors. By twisting the glass plates so that the directors are not-parallel, a helical structure of liquid crystal molecules is formed between the glass plates. For example, the standard 90° twisted nematic (TN) cell is formed with a twist angle between the molecule alignment directions of the glass plates of 90°. The molecules of liquid crystal normally used in this context, have an inherent positive dielectric anisotropy and can therefore be predominantly aligned upon the application of an electric field with a voltage higher than a cell specific threshold value. The helical molecule structure in the cell is dissolved under the electric influence and the crystal molecules are instead oriented according to the electrical field. When placed between polarisers, the transmission density of such a cell assembly can be controlled by varying the applied electrical field above the threshold voltage, whereby the transmission characteristic is typically asymptotic. The mentioned optical angular asynmmetry, however, appears in this electrically activated state.

Impurities in a liquid crystal cell tend to interfere with the liquid crystal structure, and in particular the presence of seemingly unavoidable alkaline earth metal ions causes, in the electrically activated state, a leakage current flow across the cell. If the switching of a cell is driven with a DC or low frequency voltage, such impurity ions can migrate towards the alignment layers and become embedded at the inner cell surfaces. Upon removal of the driving voltage, an electrical field across the crystal may still exist due to captured ions and may affect cell switching, therefore, liquid crystal cells are normally driven with an alternating voltage, for example a square wave voltage, where the polarity is rapidly switched in order to prevent impurity ion migration and ensuing cell degradation. Under these conditions the cell approximates to a parallel plate capacitor and must continually be charged and discharged upon polarity reversal. The leakage current flow together with the continual charging and discharging of the cell result in a large power consumption in the electrically activated state.

In the U.S. Pat. No. 5,315,099 to Gunz et al it is suggested to reduce the power consumption of a liquid crystal cell, which comprises a corrosion resistant layer and a corrosion-neutral liquid or corrosion inhibiting additives, by applying a relatively low frequency voltage in the range of 0.1 Hertz. For the purpose of reducing the cell's sensitivity to changes of the optical density due to temperature fluctuations and instabilities of the voltage source, the cell is operated at a driving voltage much higher than the threshold voltage, which also has a moderating effect on the optical transmission asymmetry for the two voltage polarities. However, the liquid crystal cell as described in U.S. Pat. No. 5,315,099 is driven at a voltage considerably higher than is required to reach the range of the asymptotic peak value of the transmission density, and consequently this cell is basically a two-state shutter.

Other drawbacks of powering a liquid crystal cell with low frequencies or even a direct current are for example decreased useful life, electrochemical changes and charging of layers within the cell structures. In particular, when using driving voltages close to the threshold voltage, the charging effects result in an optical asymmetry and a time dependent transmission. These drawbacks are also confirmed by technical specifications from manufacturers of liquid crystal cells, where it is stated that only a very low direct current component can be accepted.

In this context, a typical cell construction consists of a twisted nematic (TN) type liquid crystal cell inserted between two mutually crossed polarisation filters, where the defining walls are treated with a plastic layer which has been brushed or rubbed in specific directions, the so-called alignment directions, so that the structure in the liquid crystal defining surfaces will force the nematic molecules to each take specific angular positions and so that the molecules will be twisted mutually through 90°20 between said defining surfaces. Other surface treatment methods which have corresponding effects are also known to the art. In an electrically non-activated state, the polarisation plane will be rotated through 90° as light passes through the filter and the cell becomes transparent. This rotation of the nematic molecules can be stopped to a greater or lesser extent, by applying an electric field and therewith obtain a filter effect that can also be controlled. However, a cell of this kind has a relatively strong angular variation of transmittance in its dark, electrically activated state, with varying absorption of light that is incident at angles other than a right angle, this asymmetry being further amplified by the fact that the nematic molecules nearest the surface, bound by the surface effect, still give rise to a residual optical activity. Thus, when the angles of incident light increase in relation to the normal (i.e. the perpendicular), the filter in the two bisectrix directions between the alignment directions will be more transparent and relatively constant in relation to the directions of the crossed polarisers along the direction of one bisectrix while darkening along the direction of the other bisectrix.

It is known to compensate for the transmittance variation effect by combining two TN cells which twist through 90°, such that the "weak" bisectrix of one TN cell will coincide with the bisectrix of the other "strong" bisectrix, and vice versa. However, despite this compensation, the field of vision is still uneven, which is troublesome to the user.

An improvement in respect of the angular dependent transmission asymmetry is provided by the technology described in the copending but not yet published patent applications SE 9401423-0 and corresponding PCT/SE95/00455. These documents show a liquid crystal cell construction comprising two nematic-type liquid crystal cells, each cell being provided with molecule orientating plates defining the molecule alignment directions with mutual angular displacement in an inactivated state and electrically actuatable molecule alignment means for controllable molecule alignment in an activated state. The liquid crystal cells are each mounted between mutually extinguishing polarisation filters and the molecule alignment directions of the cells are so turned as to obtain a compensating effect between the respective asymmetrical light absorptions of the cells when a voltage is applied. The problem of angular dependent transmission is according to these patent applications reduced by at least one of the cells between the molecule alignment directors that is smaller than the previously known twist angle of 90°. In order to be able to apply the same voltage to two different liquid crystal cells, and therewith simplify the electronics required, it is in the SE 9401423-0 and PCT/SE95/00455 technology advantageous to use two mutually identical cells.

The described also provides an improvement with regard to low absorption in the transparent state of the shutter construction. Furthermore, this shutter construction applied for example in a protective welding glass will have variable darkness in its darkened state, so as to enable the same protective glass to be used with very strong welding light and with much weaker welding light, so that all types of welding work can be carried out with one and the same protective glass shield to the best possible extent. It was previously known to the art that the optical activity can be varied by applying different voltages, although the unevenness in the angle-dependent transmission density tends to become more troublesome when the voltage across the cells is increased in the earlier known techniques.

One of the problems encountered when using cells having a smaller twist angle than 90°, referred to conveniently as "low-twist cells", resides in achieving high light transmission in the transparent state while, at the same time, obtaining a sufficiently low light transmission in the dark state. Consequently, in accordance with one aspect of the SE 9401423-0 and PCT/SE95/00455 technology, a "symmetric" polarisation filter placement is preferred. When the polarisation filters are disposed at mutually intersecting angles of 90°, it is suitable to mount a low-twist cell such that the bisectrix between the surface treatment directions will coincide essentially with a bisectrix between the polarisation directions of the filters. The greatest transmission of light will then be obtained in the electrically non-activated state of the device, i.e. its transparent state.

In accordance with one embodiment of the SE 9401423-0 and PCT/SE95/00455 technology, it is convenient also to reduce the thickness of the liquid crystal cells. This results particularly in a reduced switching time, because the switching time is inversely proportional to the square of cell thickness. Thus, the switching time can be reduced in the order of magnitude of 50%, by reducing the thickness of the liquid crystal cells from 4 mm to 3 mm under otherwise equal conditions. This reduction in cell thickness is also required when low-twist cells, by virtue of a dependency that has been found to exist between the value thickness multiplied by optical anisotropy, the twist angle and the light transmission in the light or transparent state. This dependency can be utilised to construct a protective welding glass which has good optical angular properties, high light transmission in the transparent state, and rapid state-switching properties. This is only possible by using low-twist cells with the polarisation filters placed in the aforedescribed symmetric manner.

The fundamental cause of this thickness problem is that a cell which does not have appreciable thickness will not function to cleanly rotate optically incident polarised light, and elliptically polarised light will be emitted instead. When this cell is placed between two mutually crossing polarisation filters, transmission will vary periodically with the thickness of the cell.

In accordance with another embodiment of the SE 9401423-0 and PCT/SE95/00455 technology, a low-twist cell can be placed anti-symmetrically, meaning that the direction of the bisectrix of the acute angle between the treated molecule alignment directions of the cell (rubbing directions) is placed so as to coincide with the direction of polarisation of one of the mutually crossed polarisers. In a non-activated state, such a construction will exhibit relatively low light transmission, but a more transparent state is obtained when a moderate voltage is applied, this more transparent state returning to a generally darker state when the voltage is again increased. One advantage with this construction is that a loss in voltage will not result in a loss of light absorption and that a given protective effect will remain. This enables the existing standard for protective welding glass which requires the difference between an adjusted state and a state which occurs upon the loss of current supply to be at most nine darkness degrees to be maintained more easily, even at high degrees of darkness. This enables two asymmetric low-twist cells with polarisers placed anti-symmetrically to be used, or one cell with symmetrically placed polarisers and one low-twist cell with anti-symmetrical polarisers.

The low twist technology taught in SE 9401423-0 and PCT/SE95/00455 remedies the angular dependency problem of a liquid crystal cell construction and also provides a construction with voltage dependent, variable transmission density, but with state of the art electric driving methods the power consumption is still relatively high.

The problem to be solved by the present invention, and thus an object of it, is to achieve a liquid crystal shutter with variable transmission density and improved angular properties, i.e. reduced angular dependency of transmission density, together with low power consumption.

Further objects of the present invention is to provide a glare shielding device and a welding glass construction with variable transmission density and improved angular properties, together with low power consumption.

SUMMARY

According to the invention, the problem is solved and the objects achieved by means of a low twist liquid crystal cell construction driven with a low frequency or DC voltage. The general principle of the solution to the problem is to modify the electro-optic characteristics of the cell construction, so that the difference between the value of the driving voltage required for a specific transmission (optical) density and the threshold voltage is larger than previously known. In other words, the asymptotic transmission characteristic dependent on applied voltage is extended to a wider voltage range. As a consequence, the voltage used in practice to control the transmission is varied in a wider range at higher values than state of the art, thereby minimising the restraints of low frequency driving voltages.

Thus, in accordance with one aspect of the invention, for the purpose of altering the transmission characteristic of a liquid crystal cell construction, the concept moves away from the previously known typical twist angle of 90° in "twisted nematics" and, instead, employs a smaller angle which is smaller than 85°, and which preferably lies between 20° and 85°, and in some embodiments even in the range from 0° to 20°. Although the optical transmission viewing asymmetry becomes more accentuated with each individual cell, an improved field homogeneity is nevertheless obtained when two such crystals are combined.

Other aspects of the invention concern variable transmission density and power consumption and, hitherto, such a cell combination has been operated with a high frequency driving voltage according to the well known liquid crystal specifications and in order to avoid the above mentioned drawbacks of low frequency driving voltages. By extending the transmission characteristic in a low twist construction, the transmission density value in the upper dark range can be varied by means of a higher driving voltage and, in accordance with the present invention, it has now been found that this fact allows a lower frequency of the driving voltage. For welding glass filter applications, the transmission density value or shade numbers are defined conventionally as $D=1+ 7/3 \times {}^{10}\log(I/T)$, where T is the transmission coefficient, and for practical purposes the critical values are in the range of 9–14. Thus, preferred embodiments of the inventive shutter construction is driven with a voltage frequency lower than 1 Hertz or even with a DC voltage, the polarity of which is then switched at a presettable rate.

BRIEF DESCRIPTION OF THE DRAWINGS

The invention will now be described in more detail with reference to exemplifying embodiments thereof and also with reference to the accompanying drawings, in which.

DETAILED DESCRIPTION OF EMBODIMENTS

Figure 1:
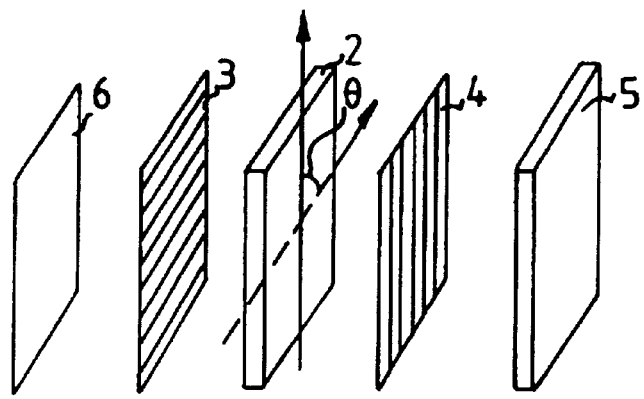
FIG. 1 is an exploded view of a previously known liquid crystal shutter construction comprising 90° twisted nematic cells.

The principle exploded view of FIG. 1 shows the various components of a protective welding glass. The outermost component is an interference filter I which also functions to eliminate UV light and IR light and limits the wavelength range. There then follows a first polarisation filter 2 or polariser, a first optically rotating liquid crystal cell 3, a second polarisation filter 4 whose polarisation direction is at right angles to the polarisation direction of the first polarisation filter 2, a second optically rotating liquid crystal cell 5, and a third polarisation filter 6 which has the same direction of polarisation as the first polarisation filter 2. The arrangement may optionally also include a so-called guest-host-cell 7. This latter cell is not an optically rotating cell but instead includes a nematic liquid crystal, whose molecules are normally aligned parallel with the polarisation direction of the third polarisation filter with the aid of prepared glass surfaces. In mixed dichroic dye molecules having ordered anisotropic absorption is highly absorbent in the aligned state. When a voltage is applied, the molecules of the nematic crystal will position themselves at right angles to said surfaces and therewith cause the molecules of the dichroic dye to move to orientations in which the least amount of light is absorbed. Cells of this kind are known to the art. One advantage afforded by such cells over other cells is that they will provide a filter effect in the absence of an applied voltage, whereas the other cell is light-transparent in the absence of an applied voltage. When such a shutter construction applied to a welding filter is taken into use, its control circuits are activated and a voltage is applied to the guest host cell 7, the filter becomes more open to light. A sensor (not shown) can now detect whether or not welding light enters the filter, wherewith the control circuit (not shown) causes a control voltage to be applied to the cells 3 and 5 while elimninating the voltage to the cell 7. An arrangement of this kind is common to both the invention and to the earlier known technique, insofar that the invention is concerned with the nature of the liquid crystals.

The inwardly facing glass plates of the cells are provided with transparent electrically conductive electrode layers (e.g. indium-tin oxide layers) on which there is applied, for instance, a polyimide layer which has been treated mechanically, normally by brushing/rubbing in specific directions, according to known techniques in directions that are perpendicular in mutually facing surfaces. According to this known technique, the cells 3 and 5 are aligned oppositely in relation to one another, for instance so that the first cell surface that receives light in the cell 3 is treated in a direction lying antiparallel to the first surface that receives light cell 5. The compensation described in the introduction is achieved herewith.

A prior art welding glass filter arrangement of this kind can be caused to change from its transparent state having a density of about 3 to density values ranging from 9 to 14, by varying the applied voltage between about 3 volts and about 5 volts. Normally the same voltage is applied to both cells.

The density varies because the voltage that strives to orientate the nematic molecules parallel with the electric field is counteracted by the plastic layers on the inner surfaces of the glass, which cause the molecules to be aligned parallel with the surfaces, and consequently the electrically influenced orientation has its greatest effect in the centre of the cell and decreases towards said surfaces. However, in practice, a certain optical activity will always remain due to the surface effects.

The transmission density or shade value is defined according to welding standards as $$D = 1 + 7/3 \times {}^{10}\log(I/T),$$

where T is the transmission value.

Despite the compensation that is achieved with regard to oblique angles of incidence, the not insignificant differences in the field of vision still remain when practicing this known technique.

Figure 2:
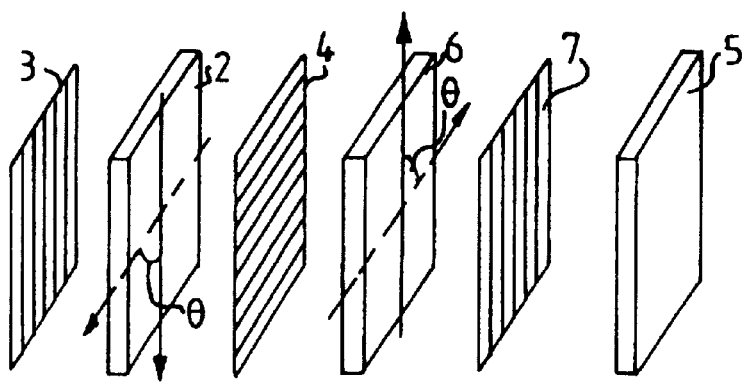
FIG. 2 illustrates two liquid crystal delimiting plates of a liquid crystal cell in accordance with the invention.

The concept of liquid crystal protective welding glass structures has in previously known art been based on the expected natural geometry that is obtained when orientation of the crystal is twisted through an angle of 90° in response to forced conditions at the boundary surfaces. An improvement can be achieved by reducing the angle through which the crystal is twisted. This is illustrated in FIG. 2, which shows a pair of plates of a liquid crystal cell. The mutually facing surfaces of the plates 10 and 11 are each provided with electrically conductive layers and thin plastic coatings. These layers and coatings are brushed, or rubbed, in accordance with the white arrows 12 and 13 but at a mutual angle q. According to the earlier known technique, this angle is 90° but is smaller than 90° according to the present invention. As illustrated, the plate arrangement is intended for a cell which rotates naturally in an anti-clockwise direction, although cells which rotate in a clockwise direction are also known. The plates are provided at 14 and 15 with means through which a voltage can be applied. The reference numerals 16 and 17 identify identification marks made on the plate edges.

A liquid crystal shutter in accordance with the invention applied as a filter in a protective welding glass included in a welding helmet, is seen by the wearer of the helmet as a shaded window. The filter is activated and has an optical density in the forward direction, this optical density, however, having an angular variation. As has been shown in SE 9401423-0 and PCT/SE95/00455, the filter effect obtained will be far more uniform over varying angles of view when the angle q differs from 90° than with state of the art 90° twisted nematic cells.

The use of two identical liquid crystal cells entails the advantage that both cells can be driven with one and the same voltage, which voltage can be varied to produce different densities. This simplifies the electronics that are required. However, this forced condition no longer applies when more expensive electronics are used, such electronics providing more degrees of freedom for obtaining said compensation.

Figure 6:
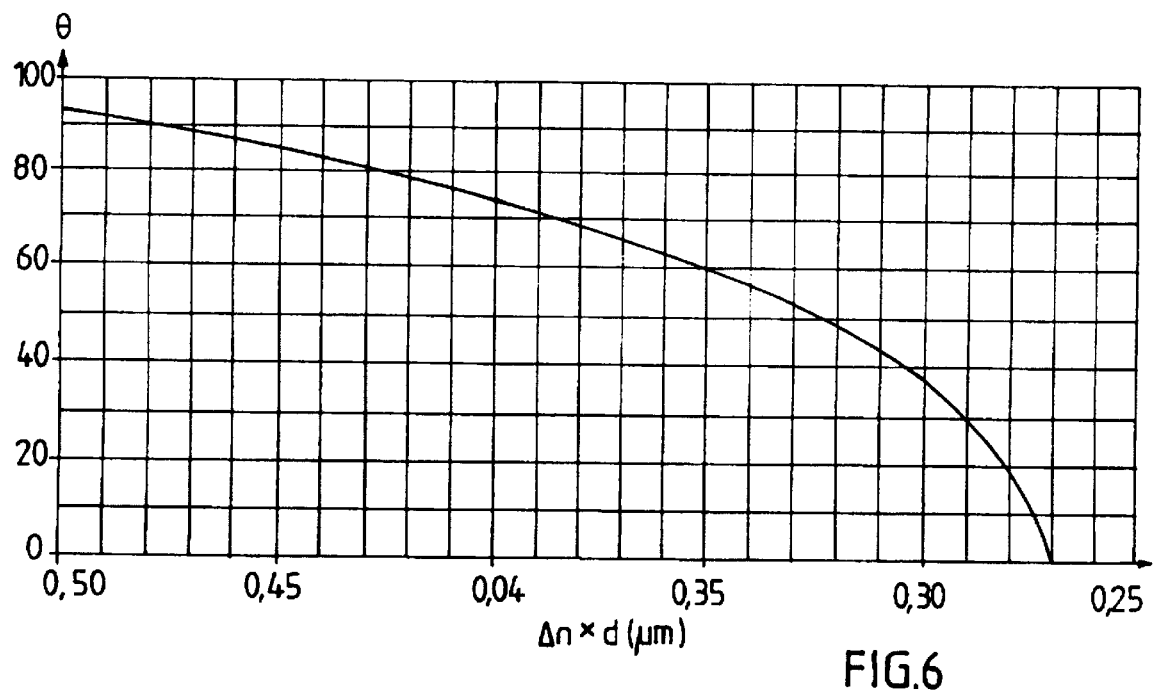
FIG. 6 illustrates how the optimal twist angle varies with the product between the optical anisotropy and the cell thickness.

As earlier mentioned, there is good reason not only to reduce the twist angle but also to reduce the thickness of the cell to a corresponding extent. It is found that there exists an optimal thickness (or more correctly an optimal product between optical anisotropy and thickness) for each twist angle, and the relation is shown in FIG. 6. The best possible transparent state is obtained at this optimal thickness.

Figure 3:
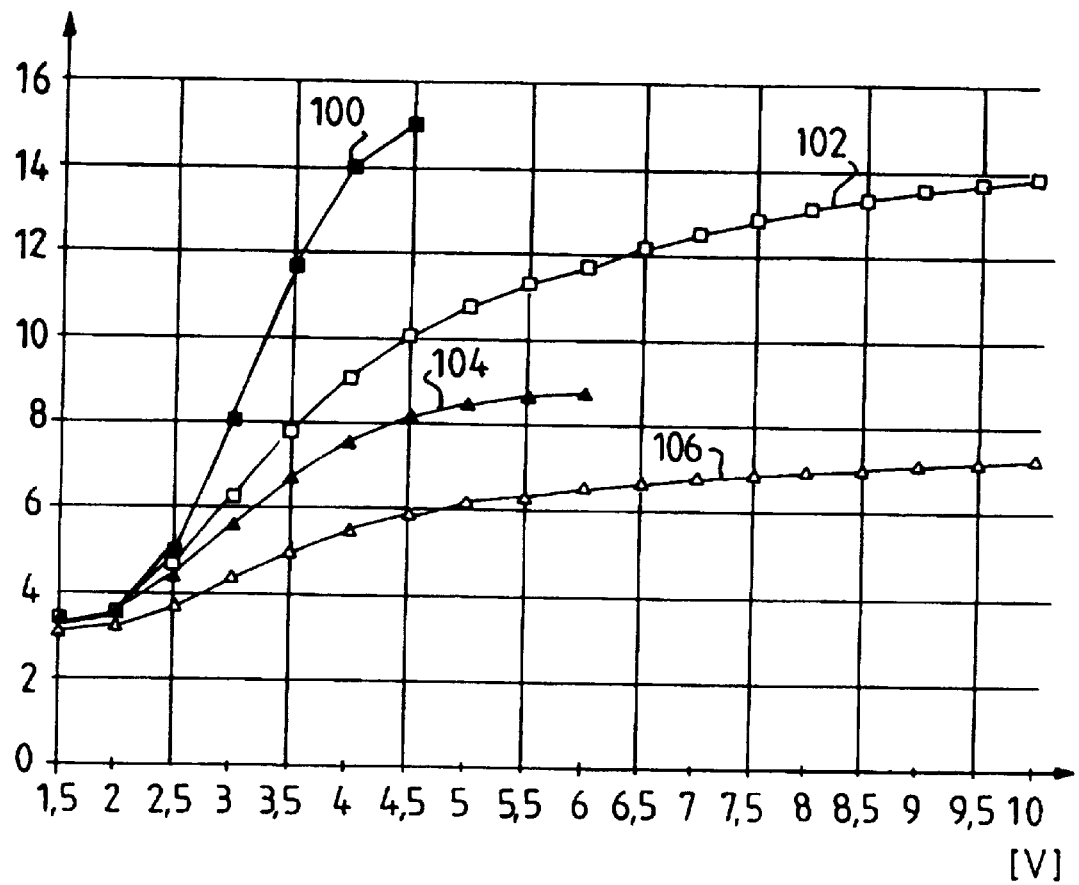
FIG. 3 shows transmission characteristics of different liquid crystal cell combinations.

According to the invention, the driving voltage shall be supplied at a low frequency and a voltage significantly higher than the threshold voltage for liquid crystal cell material. For the liquid crystal cell construction to be variable in the dark state, this requires a transmission characteristic that is extended over a wide voltage range. FIG. 3 shows the relation between transmission density or shade number and applied voltage for different liquid crystal cell combinations. Curve 100 describes the characteristic of a two-cell combination with 90° twist-angle and curve 102 two-cell combination with 70° twist-angle, whereas curves 104 and 106 show single cells with 90° and 70° twist-angles, respectively. It is clear from the diagram that the lower twist-angle, the higher voltage range between the transmission minimum at about 1.5 volts and the asymptotic transmission maximum for each cell variety.

Figure 4A:
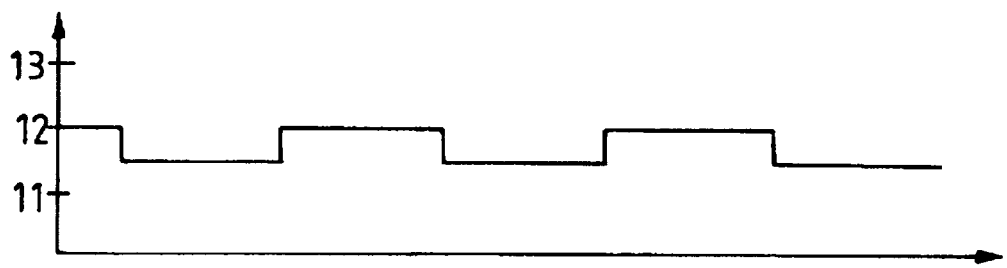
FIG. 4a, 4b and 4c show examples of transmission asymmetry effects for prior art shutter constructions.
Figure 4B:
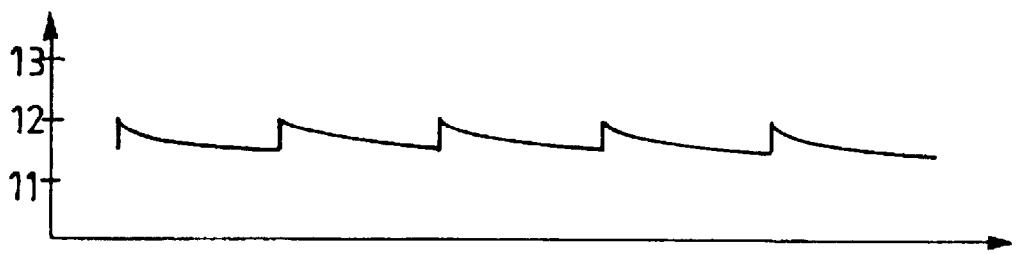
Figure 4C:
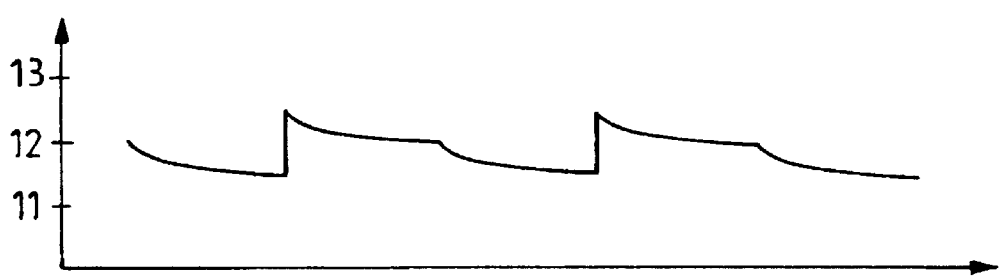

FIG. 4a, b and c show the typical effect of polarity dependent transmission asymmetry when operating a state of the art liquid crystal shutter at a low frequency, the steps of the curves occurring in connection with each polarity reversal. FIG. 4a shows a transmission asymmetry effect caused by a permanent charging effect; FIG. 4b an optical asymmetry effect caused by a charge formation during the polarity switch interval, which charge gradually reduces the effective voltage over the liquid crystal layer; and FIG. 4c shows a typical combination of the two effects. The specific transmission values of the asymmetry effect are strongly dependent on the material used in the liquid crystal cell as well as on the operating conditions.

Figure 4D:
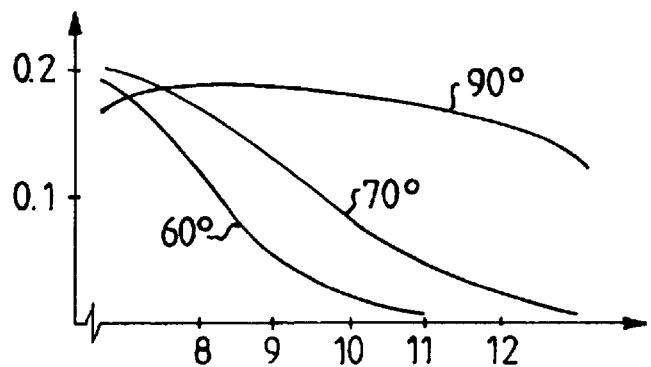
FIG. 4d shows the degree of transmission asymmetry resulting from low frequency operating for different transmission density values and different inventive cell combinations compared to prior art.

FIG. 4d shows in a diagram of test results the degree of transmission asymmetry for different transmission density values and different inventive low twist cell combinations compared to prior art 90° twisted nematics when driven with low frequency polarity reversed DC voltage. The transmission density value, or shade number, is indicated on the horizontal axis of the diagram, and the asymmetry rate is indicated on the vertical axis. The asymmetry rate is here expressed as the difference between the shade number attained with two different applied voltage polarities.

It is clear from FIG. 4d that the asymmetry rate for a certain density value is considerably lower for twist angles of for example 60° or 70° than for a twist angle of 90°. So is for example the asymmetry rate for the density value 10 between 2 and 3 times lower with a twist angle of 70° than with 90°. A similar comparison for the density value 12 shows that the asymmetry value is 5 to 10 times lower with 70° twist angle. The improvements are even better for the lower twist angle 60°. Reduction of twist angles below 60° results in a further reduction of the asymmetry degree, and then the required driving voltage is increased.

Figure 5A:
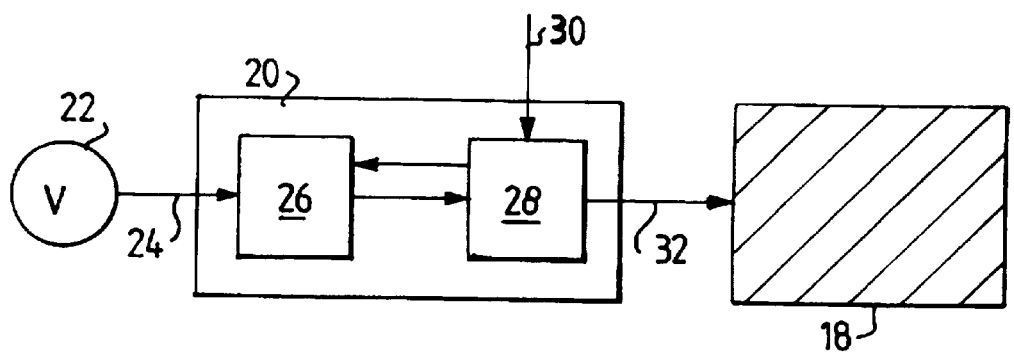
FIG. 5a and 5b are block diagrams illustrating embodiments of electric circuits for operating a liquid crystal shutter in accordance with the invention.

FIG. 5a and b are block diagrams illustrating embodiments of an electric circuit 20 for operating a liquid crystal shutter 18 in accordance with the invention. FIG. 5 shows general components of such an electric operating circuit, comprising a controllable voltage polarity switch, which is connectable to a voltage source 22 via a voltage input 24. The voltage polarity switch 26 is coupled to a cell driving voltage control means 28 having a control signal input 30 and being coupled to the liquid crystal shutter 18. The electronic circuit 20 is devised to produce a cell driving voltage substantially higher, for example 1.5 to 10 times higher for the darkest state, than the threshold voltage of the liquid crystal material of the cells in the shutter.

Figure 5B:
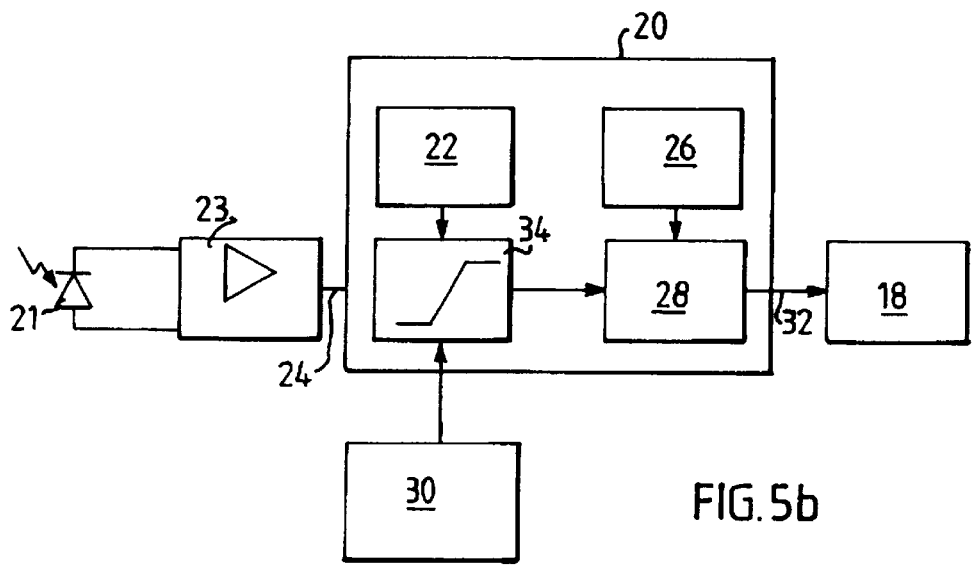

FIG. 5b shows another embodiment of the electric operating circuit 20 of FIG. 5a. A direct current voltage source 22 is in FIG. 5a connected to a voltage regulator 34, which itself is connected to a driver circuit 36. The driver circuit 36 is connected to polarity switch in the form of an oscillator or a flip-flop circuit that controls the drive frequency or the polarity of the voltage supplied to the liquid crystal cell 18 from the driver circuit 36. This embodiment is provided with two control signal inputs, firstly an light detector input 24 and secondly a transmission density control input through which the resulting shading if the shutter is selectable. An ambient light detector 22 comprising a photosensitive sensor 21 is conveniently coupled to the ambient light detector input 24.

The polarity of the driving voltage may, for example, be switched at a presettable rate, or alternate in response to each detected sudden increase in ambient light. The latter being suitable for the welding glass filter application.

Due to both a low twist angle and a reduced Δn*d parameter, the optical angular properties of the 0° birefringent cell with Δn*d in the range of 0.27 micrometers are found to be highly favourable and clearly suitable for both a single cell and a double cell liquid crystal shutter construction that requires a wide and symmetrical viewing field. Due to the large remnant retardation present in the 0° cell when driven at voltages less than 10 volts, the available cell contrast from such a device is found to be small in comparison to that for a 90° twisted nematic liquid crystal cell. In accordance with an embodiment of the invention, the cell contrast is improved by means of an addition of a compensating retardation film. In the 0° birefringent cell embodiment a small retardation value of about 25 to 30 nm is appropriate. In order to maximize the compensation effect, the retardation film should preferably be aligned such that the fast axis direction is perpendicular to the entrance and exit molecular director vectors of the cell. The compensating retardation layer for the 0° birefringent cell can for example be in the form of a single, uniaxial retardation film, with a value of between 10 to 50 nm. In another embodiment, the compensating retardation layer may be implemented by means of retardation films that are aligned such that the net overall retardation generated by the films is within said interval. With, for example, a 27 nm compensating retardation film applied in the shutter construction, the optimum Δn*d value of the cell combination is increased from about 0.27 micrometers to 0.277 micrometers.

FIG. 6 illustrates how the optimal twist angle varies with the product between the optical anisotropy and the cell thickness.

Figure 7:
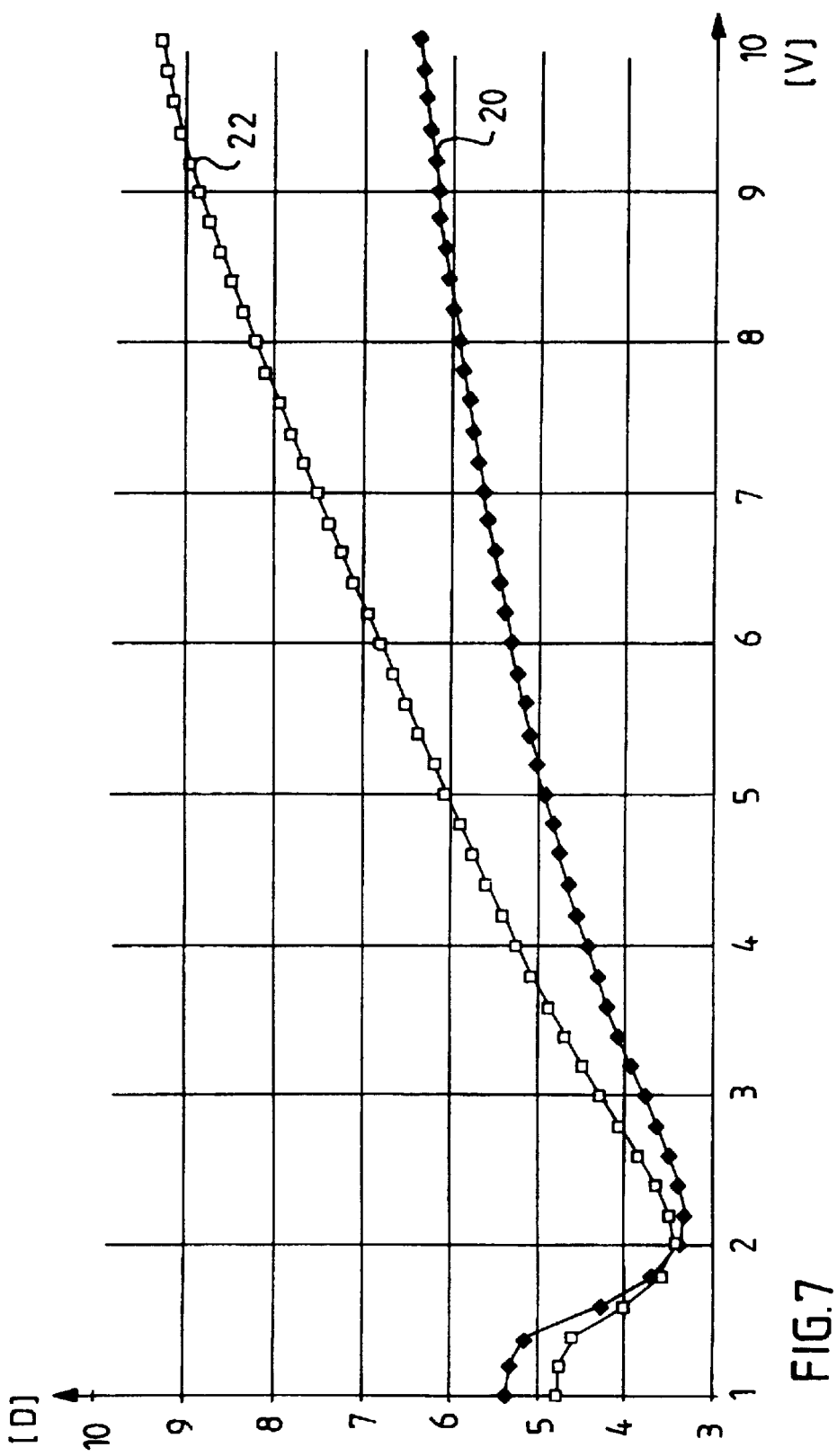
FIG. 7 shows the transmission characteristics of a device according to the invention, including a retardation film and the transmission characteristics of the device without any compensating retardation film.

FIG. 7 shows the electro-optic properties of a liquid crystal construction including a 4 micrometer 0° birefringent cell. The birefringent cell, in this instance comprising the Merck ZLI-4246 liquid crystal giving a Δn*d value of about 0.52 micrometers, is placed between mutually crossed polarisers aligned at 45° and 135° relative to the entrance molecular director vector. The cell is, in correspondence with one embodiment of the invention, placed together with a band pass filter that has a high optical transmittance over the central part of the visible spectrum, that is in the range of 500 to 600 nm. Curve 20 shows the optical response of the cell combination without any compensating retardation film, whereas curve 22 shows a cell combination including a 26 nm compensating retardation film oriented such that the fast axis is perpendicular to the entrance molecular director. The improvement in cell contrast with the compensation retardation film is clearly seen in this figure.

Figure 8A:
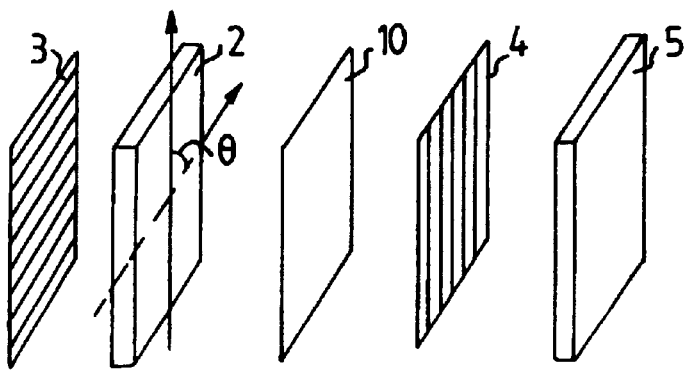
FIG. 8 shows the in principle an embodiment of the invention provided with a retardation film.

FIG. 8 shows the in principle an embodiment of the invention provided with a retardation film positioned on one side of one of the liquid crystal cell 2 between the polarisation filters 3 and 4. It is also possible to place a retardation film within the liquid crystal cell 2 between the molecular alignment directing plates.

What is claimed is:

1. A liquid crystal shutter construction (18), suitable for a glare shield or a welding glass filter, which shutter construction is able to switch between a high light-absorbing dark state and a low light-absorbing transparent state, and vice versa, in response to an electric signal and which includes two nematic-type liquid-crystal cells disposed between transparent, electrode-loaded plates connectable to a voltage source (22) and which cells are provided with coatings treated to define the direction of molecule alignment at their mutually facing surfaces, whereby a mutual angular displacement between said plates causes the liquid crystals to form a twisted helix structure in the absence of a voltage between the electrode coatings on the plates, wherein the cells are each mounted between mutually extinguishing polarisation filters, and wherein the molecule alignment directions are turned so as to obtain a compensation effect between the respective asymmetrical light absorptions of the two cells when a voltage is applied, wherein at least one of the twisting angular displacements of the cells between said molecule alignment directions differs from 90°, the shutter construction comprising means (20) for generating a variable cell driving voltage applicable to said electrode-loaded plates, said means (20) being devised to produce a cell driving voltage higher than twice the threshold voltage for at least one of the liquid crystal cells and with a polarity switching frequency of less than 1 Hertz.

2. A shutter construction according to claim 1, wherein the angle between the alignment directions is such that the transmission density value or shade number of the shutter is variable in the range of 9 to 15 with a cell driving voltage higher than twice the threshold voltage for at least one of the liquid crystal cells.

3. A shutter construction according to claim 1, wherein the angular displacement between the alignment directions of at least one of the cells has an angle of between 0° and 85°.

4. A shutter construction according to claim 1, wherein the thickness of the liquid crystal cell, which differs from a 90° angular twist between said alignment directions, is so adapted that the product of the thickness and the difference between the highest and the lowest refractive index of the liquid crystal material for different polarisation directions is at most 0.4 mm, and that each cell has an angular difference between said molecular direction determining coatings of at most 70°.

5. A shutter construction according to claim 4, wherein said thickness is at most 0.3 mm.

6. A shutter construction according to claim 1, wherein the two cells are essentially identical, and in that the voltage source is adapted to apply equal voltages to the cells.

7. A shutter construction according to claim 1, wherein the polarisation filters between which the respective cells are mounted have polarisation directions which cross one another at an angle of 90°.

8. A shutter construction according to claim 1, wherein at least one of the cells, whose molecule alignment direction defining coatings have a mutual angular displacement below 90°, is mounted between polarisation filters whose polarisation directions coincide with the directions of the respective nearest coatings.

9. A shutter construction according to claim 1, wherein the bisectrix of the acute angle between the alignment directions that differ from 90° is generally parallel with a bisectrix between the polarisation directions of the two surrounding polarisation filters.

10. A shutter construction according to claim 1, wherein at least one of the liquid crystals has a relationship between, on the one hand, the product of the thickness and the difference between the highest and the lowest refractive indexes of the liquid crystal cells for different polarisation directions and, on the other hand, the angle between said alignment directions which corresponds to a point on the curve shown in FIG. 6.

11. A shutter construction according to claim 1, wherein for at least one of the cells the angular displacement between the alignment directions presents an angle between 0° and 50°, and in that a retardation film is disposed in connection to the liquid crystal cells.

12. A shutter construction according to claim 1, wherein the means for generating a variable cell driving voltage comprises an electronic circuit (20) being provided with a voltage input (24) connectable to a voltage source (22), a voltage polarity switching means (26) for controlling the polarity of an output cell driving voltage, said voltage polarity switching means (26) being coupled to a driving voltage control means (28) which is provided with a control signal input (30) and which is coupled to a cell driving voltage input (32).

13. A shutter construction according to claim 1, wherein the means (20) for generating a variable cell driving voltage is provided with a detector input (24) being connectable to an ambient light detector (22), and in that it comprises a voltage regulator (34) being connectable to a shade select means (30).

14. A crystal shutter construction according to claim 1, wherein the voltage polarity switching means is an oscillator or a flip-flop circuit.

15. A shutter construction according to claim 1, wherein the shutter construction is a welding glass filter applied in a welding glass shield, or wherein the shutter construction is applied in an optical instrument, such as an optical amplifier telescope or binoculars.

16. A liquid crystal shutter construction (18), suitable for a glare shield or a welding glass filter, which shutter construction is able to switch between a high light-absorbing dark state and a low light-absorbing transparent state, and vice versa, in response to an electric signal and which includes two nematic-type liquid-crystal cells disposed between transparent, electrode-loaded plates connectable to a voltage source (22) and which cells are provided with coatings treated to define the direction of molecule alignment at their mutually facing surfaces, whereby a mutual angular displacement between said plates causes the liquid crystals to form a twisted helix structure in the absence of a voltage between the electrode coatings on the plates, wherein the cells are each mounted between mutually extinguishing polarisation filters, and wherein the molecule alignment directions are turned so as to obtain a compensation effect between the respective asymmetrical light absorptions of the two cells when a voltage is applied, wherein at least one of the twisting angular displacements of the cells between said molecule alignment directions differs from 90°, the shutter construction comprising means (20) for generating a variable cell driving voltage applicable to said electrode-loaded plates, said means (20) being devised to produce a cell driving voltage higher than twice the threshold voltage for at least one of the liquid crystal cells.

17. A liquid crystal shutter construction (18), suitable for a glare shield or a welding glass filter, which shutter construction is able to switch between a high light-absorbing dark state and a low light-absorbing transparent state, and vice versa, in response to an electric signal and which includes two nematic-type liquid-crystal cells disposed between transparent, electrode-loaded plates connectable to a voltage source (22) and which cells are provided with coatings treated to define the direction of molecule alignment at their mutually facing surfaces, whereby a mutual angular displacement between said plates causes the liquid crystals to form a twisted helix structure in the absence of a voltage between the electrode coatings on the plates, wherein the cells are each mounted between mutually extinguishing polarisation filters, and wherein the molecule alignment directions are turned so as to obtain a compensation effect between the respective asymmetrical light absorptions of the two cells when a voltage is applied, wherein at least one of the twisting angular displacements of the cells between said molecule alignment directions differs from 90°, the shutter construction comprising means (20) for generating a variable cell driving voltage applicable to said electrode-loaded plates, said means (20) being devised to produce a cell driving voltage higher than twice the threshold voltage for at least one of the liquid crystal cells, wherein the cell driving voltage is an alternating current voltage.

18. A shutter construction according to claim 17, wherein the cell driving voltage has a polarity switching frequency of less than 1 Hertz.

19. A liquid crystal shutter construction (18), suitable for a glare shield or a welding glass filter, which shutter construction is able to switch between a high light-absorbing dark state and a low light-absorbing transparent state, and vice versa, in response to an electric signal and which includes two nematic-type liquid-crystal cells disposed between transparent, electrode-loaded plates connectable to a voltage source (22) and which cells are provided with coatings treated to define the direction of molecule alignment at their mutually facing surfaces, whereby a mutual angular displacement between said plates causes the liquid crystals to form a twisted helix structure in the absence of a voltage between the electrode coatings on the plates, wherein the cells are each mounted between mutually extinguishing polarisation filters, and wherein the molecule alignment directions are turned so as to obtain a compensation effect between the respective asymmetrical light absorptions of the two cells when a voltage is applied, wherein at least one of the twisting angular displacements of the cells between said molecule alignment directions differs from 90°, the shutter construction comprising means (20) for generating a variable cell driving voltage applicable to said electrode-loaded plates, said means (20) being devised to produce a cell driving voltage higher than twice the threshold voltage for at least one of the liquid crystal cells, wherein the cell driving voltage is a direct current (DC) voltage.

20. A shutter construction according to claim 19, wherein the polarity of the cell driving voltage is switched at selectable intervals.

21. A shutter construction according to claim 19, wherein the polarity of the cell driving voltage is switched at a presettable rate.

22. A shutter construction according to claim 19, wherein the polarity of the cell driving voltage is switched in response to a selected event, e.g. in response to a detected increase in ambient light.

23. A shutter construction according to claim 19, wherein the polarity switching frequency of the cell driving voltage is less than 1 Hertz.

* * * * *